United States Patent
Macpherson et al.

(10) Patent No.: US 8,409,410 B2
(45) Date of Patent: Apr. 2, 2013

(54) CONDUCTIVITY SENSOR DEVICE COMPRISING DIAMOND FILM WITH AT LEAST ONE NANOPORE OR MICROPORE

(75) Inventors: Julie Macpherson, Coventry (GB); Patrick Unwin, Coventry (GB); Mark Newton, Coventry (GB); Henry White, Salt Lake City, UT (US)

(73) Assignees: University of Warwick, Coventry (GB); University of Utah Research Foundation, Salt Lake City, UT (US)

( * ) Notice: Subject to any disclaimer, the term of this patent is extended or adjusted under 35 U.S.C. 154(b) by 20 days.

(21) Appl. No.: 12/927,434

(22) Filed: Nov. 15, 2010

(65) Prior Publication Data

US 2011/0120890 A1    May 26, 2011

Related U.S. Application Data

(63) Continuation of application No. PCT/GB2009/001229, filed on May 14, 2009.

(30) Foreign Application Priority Data

May 15, 2008 (GB) .................................. 0808856.9

(51) Int. Cl.
*G01N 27/414* (2006.01)
(52) U.S. Cl. ........................................ 204/400; 205/775
(58) Field of Classification Search .............. 204/403.01, 204/400; 205/775, 777.5, 792, 789, 789.5; 210/321.84, 500.22, 500.26; 216/6, 56
See application file for complete search history.

(56) References Cited

U.S. PATENT DOCUMENTS

| | | | |
|---|---|---|---|
| 6,488,829 B1 * | 12/2002 | Schroeder et al. | 204/403.01 |
| 2002/0006357 A1 * | 1/2002 | McGeoch et al. | 422/82.01 |
| 2003/0080042 A1 | 5/2003 | Barth et al. | |
| 2006/0275911 A1 | 12/2006 | Wang et al. | |
| 2007/0017437 A1 | 1/2007 | Genis et al. | |

FOREIGN PATENT DOCUMENTS

| | | | |
|---|---|---|---|
| JP | 2008-74690 | * | 4/2008 |
| WO | WO 03/066930 | | 8/2003 |
| WO | WO 2005/012894 | | 2/2005 |
| WO | WO 2007/107844 | | 9/2007 |
| WO | WO 2008/021488 | | 2/2008 |
| WO | WO 2008/042018 | | 4/2008 |
| WO | WO 2009/138760 | | 11/2009 |

OTHER PUBLICATIONS

Machine translation of JP 2008-74690, Apr. 2008.*
Dekker, C. "Solid State Nanopore", Nature Nanotechnology, 2007, 2, 209-215.
Fertig, N. et al, "Activity of single ion channel proteins detected with a planar microstructure", Appl. Phys. Lett. 2002, 81, 4865-4867.
Deamer, D. W., Branton, D. "Characterization of Nucleic Acids by Nanopore Analysis", Acc. Chem. Res. 2002, 35, 817-825.

(Continued)

*Primary Examiner* — Luan Van
*Assistant Examiner* — Gurpreet Kaur
(74) *Attorney, Agent, or Firm* — Wiggin and Dana LLP

(57) ABSTRACT

Sensor device for ion channel recordings; liquid-liquid measurements and resistive pulse particle counting comprising; at least one sensor element; the element comprising a diamond thin film substrate and a pore which is a nanopore or a micropore included in the substrate. This device may be used in analysis, for instance the device may be used for single molecule detection of an apialyte (e.g. DNA), for the analysis of interactions between a sensor element and an analyte, for the detection of pore forming entities, or for the determination of ion transfer.

13 Claims, 10 Drawing Sheets

OTHER PUBLICATIONS

Kasianowicz, J. J., Branton, D., Deamer, D.W. "Characterization of individual polynucleotide molecules using a membrane channel", Proc. Natl. Acad. Sci. 1996, 93, 13770-13773.

Bayley, H., Martin, C.R, "Resistive-Pulse Sensings From Microcrobes to Molecules" Chem. Rev. 2000, 100, 2575-2594.

Akeson et al, "Microsecond Time-Scale Discrimination Among Polysytidylic Acid, Polyadneylic Acid and Polyuridylic Acid as Homopolymers or as Segments Within Single RNA Molecules", Biophys. J. 1999, 77, 3227-3233.

White, R. J. et al "Single Ion-Channel Recordings Using Glass Nanopore Membranes", J. Am. Chem. Soc. 2007, 129, 11766-11775.

Leich, M. A., Richmond, G.L. "Recent experimental advances in studies of liquid-liquid interfaces", Faraday Discussions 129 (2005) 1.

Taylor G., Girault, H.H.J. "Ion Transfer Reactions Across a Liquid-Liquid Interface Supported on a Micropipette Tip", J. Electroanal. Chem. 208 (1986) 179.

Campbell, J.A., Girault, H.H. "Steady state current for ion transfer reactions at a micro liquid/liquid interface", J. Electroanal. Chem. 266 (1989) 465.

Zazpe, R., Hibert, C., O'Brien, J., Lanyon, Y.H., Arrigan, D.W.M. "Ion transfer voltammetry at silicon membrane-based arrays of micro-liquid-liquid interfaces", Lab on a Chip 7 (2007) 1732.

DeBlois, R.W., Bean, C.P. "Counting and Sizing of Submicron Particles by Resistive Pulse Technique", Rev. Sci. Instrum, 7 (1970), 41, 909-916.

Li, J., Gershow, M., Stein, D., Brandin, E., Golovchenko, J.A. "DNA molecules and configuration in a solid state nanopore microscope", Nat. Mater. 2 (2003) 611.

Brandon, J. R.; Coe, S. E.; Sussmann, R. S., et al. "Development of CVD diamond r.f. windows for ECHR", Fusion Eng. Design 2001, 53, 553-559.

Lee, C.L.; Gu, E. et al "Micro-cylindrical and micro-ring lenses in CVD diamond", Diamond, Rel. Mater. 2007, 16, 944-948.

Hunn, J.D.; Withdrow, S.P.; White, C.W. et al. "The separation of thin single crystal from bulk diamond by MeV implantation", Nuc. Instrum. Methods in Phys Res. B; Beam Inter. Mater. Atoms, 1995, 99, 602-605.

J.M. Taylor, P. Cappellaro, L. Childress, L. Jiang, D. Budker, P.R. Hemmer, A. Yacoby, R. Walsworth & M. D. Lukin, "High-sensitivity diamond magnetometer with nanoscale resolution", Nature Physics, 2008, 4, 810.

Deblois, R. W. and Wesley, R. K. A., "Sizes and Concentrations of Several Type C Oncornaviruses and Bacteriophage T2 by the Resistive-Pulse Technique", J. of Virology 1977, 23, 227-233.

Deblois, R. W. and Bean, C. P.; Wesley, R. K. A., "Electrokinetic Measurements with Submicron Particles and Pores by the Resistive Pulse Technique", J. Colloid Interface Sci. 1977, 61, 323-335.

Ito, T., Sun, L., Henriquez, R. R. and Crocks, R. M. "A Carbon Nanotube-Based Coulter Nanoparticle Counter", Acc. Chem. Res. 2004, 937-945.

Saleh, O. A. and Sohn, L. L. "An Artificial Nanopore for Molecular Sensing", Nano Lett. 2003, 3, 37-38.

Shim, J. H.; Kim, J.; Cha, G. S.; Nam, H.; White, R. J., White, H. S. and Brown, R. B, "Glass Nanopore-Based Ion Selective Electrodes", Anal. Chem. 2007, 79, 3568-3574.

International Search Report dated Jul. 30, 2009.

* cited by examiner

Diamond deposited on and template etched away.

CONDUCTIVITY SENSOR DEVICE COMPRISING DIAMOND FILM WITH AT LEAST ONE NANOPORE OR MICROPORE

CROSS-REFERENCE TO RELATED APPLICATIONS

This application is a continuation application of PCT/GB2009/001229 filed May 14, 2009, which claims the benefit of GB 0808856.9 filed May 15, 2008. The disclosures of PCT/GB2009/001229 and GB 0808856.9 are incorporated herein by reference in their entireties.

The invention relates to a sensor device, and to methods of using the device. In particular, the invention relates to a device including a diamond thin film substrate.

Improvements in chemical and biochemical analyses rely on new materials and methods that provide improved sensitivity, reliability and longevity. Increased temporal and spatial resolution enables analyses of biological events at the single molecule level and at very short timescales, enabling kinetic, thermodynamic, and chemical dynamic information to be obtained. To derive these advantages, new methods and materials are continually sought, with a particular emphasis on cost and manufacturability. With this in mind there has been much effort in silicon and silicon nitride microfabrication[1] and glass (to a lesser extent)[2] to make small analytical devices for mass production.

Nanopores and micropore systems are used in many different analytical applications including the detection of single molecules,[3] the detection and sequencing of DNA,[4] particle counting,[5] model drug delivery systems, liquid-liquid analysis, and screening of the interactions of new pharmaceutical drugs with protein ion channels that are found in the human body.[6] The majority of these applications rely on the measurement (often moderation) of an electrical (or electrochemical) signal, be it across an open pore, liquid-liquid interface formed at the mouth of the pore or a bilayer-modified pore. In the majority of cases the size and geometry of the pore and electrical properties of the substrate in which the pore is formed are vitally important factors which control the sensitivity of the device for chemical and biochemical analysis. The chemical stability of the substrate material determines the usefulness of the device in different environments.

Some specific applications of nanopore and micropore systems are described in the following paragraphs.

(i) Biopolymer Sequencing Using Nanopores: There have been recent reports of the use of biological nanopores e.g. α haemolysin (HL) for the detection and sequencing of biopolymers, e.g., DNA. Proof-of-concept experiments demonstrated that the number of nucleotides in single-stranded (ss) DNA could be identified by measuring the length of time the strand spent in the channel.[4] Upon application of a small potential the DNA molecules were driven through an ion channel inserted in a lipid bilayer. As the molecule moves through the pore, the current decreases due to DNA blocking the motion of the charge carrying electrolyte ions. It has been suggested that the variation in current, as DNA moves through the pore, might be used to identify the sequence of bases. Due to experimental limitations, high-speed detection of the sequence of bases in single molecules of DNA or RNA was not possible.[4]

In biosensors and chemical sensors, ion channel recordings using a protein inserted in a lipid bilayer are also useful for the detection of small molecules. The same system is used in electrophysiological investigation of protein molecule interactions, where the molecule may be a toxin or a new drug under development.

Traditionally, protein ion channel recordings have relied on the formation of bilayers across ~25-100 μm diameter orifices in thin Teflon sheets.[7] These measurements are useful for the screening of new drug molecules, and in fundamental measurements of protein biophysics. However, there are several drawbacks with this approach: (i) the large area of the supported bilayer means that the bilayer is subject to mechanical instabilities and is short lived; (ii) the high capacitance of the bilayer and the support prevents electrical readout of very fast single binding or translocation events and introduces noise. For example, it is reported that the translocation rate of ssDNA though α-HL pores is 1 to 20 μs per nucleotide, which requires data acquisition rates of nearly $10^6$ Hz. Hence to collect data at a faster rate, it is desirable to reduce the capacitance of the system; this can potentially be accomplished by reducing the bilayer area and using substrate materials that yield lower overall capacitances.

Recently a more robust glass and quartz nanopore platform has been introduced, whereby a sub-microscopic bilayer region is exposed leading to greatly extended bilayer lifetimes (~several weeks) and significant reduction in the electrical capacitance[8]. In such systems a conically shaped pore of outer diameter 100 nm-1 μm is formed in a glass or quartz membrane, using a one-at-a-time fabrication approach. Using the nanopore membrane platform for the bilayer arrangement significantly reduces the capacitance of the system.

(ii) Sensing at liquid-liquid interfaces. Ion and molecular transfer at liquid-liquid interfaces impacts in many different areas[9] of most importance are perhaps biosensing (model interface for drug analysis) and bioanalysis (monitoring of biologically important ions $K^+$, $Na^+$, $Cl^-$ and charged drug molecules—i.e. potentiometric and amperometric ion selective electrodes), although other useful applications include solvent extraction, materials synthesis and catalysis, metal, polymer and particle deposition. The liquid-liquid interface also acts as a simplified model of a biological membrane (which can be modified by lipids and surfactants, for example). Traditionally such interfaces are probed using a variety of surface techniques such as surface second harmonic generation, vibrational sum frequency spectroscopy, total internal fluorescence spectroscopy and X-Ray and neutron scattering.[11]

Electrochemistry also represents a powerful technique for the dynamical study of ion and molecular transfer across such interfaces. However, it is recognized that in order to quantify such (fast) processes experimentally the interface formed should be at the micro or smaller scale in order to stabilize the interface, minimize iR problems and increase mass transport, akin to standard solid microelectrodes.[10] Typically such approaches use a glass capillary pulled to a fine point, which is filled with the aqueous solution and placed into an organic solvent or vice versa. In some cases it is necessary to silanize the capillary to change its wetting properties. Problems arise when using sub-micron capillaries: the size of the capillary can be difficult to quantify; it is fragile and can often break; and it is difficult to control the cone angle, which plays a role in controlling the internal resistance of the capillary. Also it is difficult to obtain reproducibility between capillaries. Suitable systems for fabrication of liquid-liquid based sensors are therefore sought which are insulating, robust, can be reproducibly fabricated at the micron and sub-micron scale and can be scaled up to produce arrays of pores for increasing the magnitude of the measurement signal. The applications of these sensors would be in the areas defined above.

Various methods have been suggested as alternatives to glass capillaries. These include photo- and laser ablated holes in a polymer film,[11] track etched polycarbonate membranes and very recently silicon microlithography.[12] Most of these techniques produce holes at the micron scale.

(iii) Particle Counting: Counting particles using resistive pulse sensing is a common technique, exemplified by the Coulter counter which is a commercial device for counting and sizing colloids and biological cells.[13] The device typically employs a sapphire membrane which contains an aperture with a size ranging from ~20 μm to 2 mm. Particles with sizes in the range 2-60% of the aperture diameter can usually be detected. Electrolyte containing the species of interest is placed either side of the membrane, under galvanostatic conditions. Solution is forced through the membrane using a pressure gradient and changes in the aperture resistance due to the presence of particles are detected as increases in the trans-aperture voltage (i.e. a voltage pulse). The number of pulses can be used to determine the number of particles.

For the sensing of particles <500 nm in size there is clearly a need to move to smaller apertures. Polycarbonate membranes have been investigated[14] and there is now a wide variety of membranes employed to decrease detection sizes even further such as silicon nitride nanopores with dimensions as small as 3 nm in diameter[15] produced using ion beam sculpting techniques. However, below ~10 nm there are major reproducibility issues with the techniques and materials currently being employed. The counting and analysis of nanometer scale particles using resistive pulse sensing also requires low noise and fast data acquisition.

In accordance with a first aspect of the invention there is therefore provided, a sensor device for ion channel recordings; liquid-liquid based sensors and resistive pulse particle counting comprising,
  at least one sensor element;
  the element comprising a diamond thin film substrate and a pore which is a nanopore or a micropore included in the substrate.

The ion channel recordings are typically selected from single molecule detection, biosensors, and DNA sequencing.

The above paragraphs describe representative application areas of micropore and nanopore analytical devices. These devices and their associated methodology can be greatly enhanced through the employment of diamond as the substrate material. The unique characteristics of diamond relevant to these applications include:

(1) Chemical stability and durability: extremely high resistance to chemical attack in strong acid and alkali solutions. In addition, diamond surfaces are not prone to hydration phenomenon that occurs at silicate-based structures, e.g., glass and quartz.

(2) Electrical Properties (see Table 1): has a very high resistivity in the intrinsic state ($10^{13}$-$10^{16}$ Ωcm), very low dielectric constant (5.7), low dielectric loss tangent (<$1 \times 10^{-5}$ at 30-150 GHz[16]; measurements in the MHz range on good quality diamond are currently lacking but we envisage the loss tangent of high quality single crystal material to be as good as quartz at RF frequencies). These properties make diamond a nearly ideal material for low noise, fast data acquisition using micro/nanopore based analytical devices.

(3) Optical Properties: intrinsic diamond has excellent optical properties and is transparent in the UV (225 nm)-visible-far IR regions. These properties allow spectroscopic measurements to be combined with electrical detection of the pore conductivity.

(4) Fabrication: Polycrystalline synthetic diamond can be grown at the wafer scale, using chemical vapour deposition techniques. Using dopants such as Boron it is also possible to produce alternating layered structures with differing electrical properties. It is also possible to simultaneously manufacture large numbers of diamond based devices.

(5) Biocompatibility. Diamond is all carbon (bar surface termination) and therefore represents a biocompatible material. It also has been shown to be resistant to fouling in complex media, such as blood.

TABLE 1

Diamond Electrical Properties
(including a comparison with other materials)

|  | SiC | Silica Glass (Fused Quartz) | Silicon | Diamond |
|---|---|---|---|---|
| Breakdown voltage (V cm$^{-1}$) | $3 \times 10^6$ | $5\text{-}7 \times 10^6$ (~$5 \times 10^5$) | $0.3 \times 10^6$ | $20 \times 10^6$ |
| Electron Mobility (cm$^2$ V$^{-1}$ s$^{-1}$) | 900 |  | 1450 | 4500 |
| Hole mobility (cm$^2$ V$^{-1}$ s$^{-1}$) | 120 |  | 480 | 3800 |
| Saturation Velocity (cm s$^{-1}$) | $2 \times 10^7$ |  | $0.86 \times 10^7$ | $1.8 \times 10^7$ |
| Thermal conductivity (W cm$^{-1}$ K$^{-1}$) | 5 | 0.01 (~0.01) | 1.5 | 24 |
| Dielectric Constant | 9.72 | 3.8 (~3.75) | 11.9 | 5.7 |
| Dielectric Loss Tangent |  | 17 GHz (<$1 \times 10^{-5}$); 100 MHz~$2 \times 10^{-4}$ |  | 30-150 GHz < $1 \times 10^{-5}$ (good quality poly) $10^9\text{-}10^{12}$ Hz~ $6 \times 10^{-4}$ (natural diamond) |
| Electrical Resistivity (Ωcm) |  | $4 \times 10^9$-$3 \times 10^{10}$ ($7 \times 10^7$) |  | $10^{13}$-$10^{16}$ |
| Refractive Index | 2.7 | 1.5 | 3.5 | 2.4 |

The chemical and physical properties of diamond make it a nearly ideal substrate for application in analytical methods based on micro and nanopores. Recent challenges in the processing of diamond thin films, including the etching of 3D structures and the chemical modification of diamond surfaces, makes possible the invention disclosure below.

Diamond can be processed into many different forms, for use in different applications, some illustrative examples are outlined below:

Polycrystalline diamond films: Polycrystalline Chemical Vapour Deposition (CVD) diamond material can be prepared as thin free standing films, e.g., 10 μm thick over tens of mm×mm lateral dimensions and thick films in the form of 100 mm diameter wafers, up to a few mm thick. Thinner (1-2 μm) nanocrystalline diamond films on silicon-wafers are available commercially and areas of the silicon substrate can be etched away to leave a silicon supported nanocrystalline diamond film.

Single crystal diamond: Intrinsic single crystal diamond films are commercially available, a typical size would be about 4.5×4.5×0.5 mm although, of course, thinner, thicker, larger and smaller sizes can be produced.

Recent advances in the polishing, machining and etching of diamond now allow smooth structured surfaces to be designed and fabricated. In particular:

(i) Mechanical Polishing: Single and polycrystalline diamond >10 μm—e.g. a few mm thick can be mechanically polished with an rets surface roughness of <5 nm, and even <1 nm with more specialized techniques.

(ii) Laser Drilling: It is possible to drill holes down to around the micron level in diamond. For the smallest holes, percussion laser drilling (e.g. pulsing the focused laser in the same spot) can be employed to produce holes with exit diameters of less than ~10 μm in diamond ~300 μm thick, e.g., aspect ratio of ~30:1. For thinner diamond samples, e.g., 50 μm thick, holes of exit diameter 1-5 μm (5-10 μm entrance diameter) can be realised. Larger diameter (e.g. 20-500 μm) highly circular holes can be produced by laser trepanning.

(iii) Laser Milling: Micro-milling can be used to create 2.5 dimensional (2.5 D not quite 3 D as the laser needs to cut a path to get to the machining surface) features in the surface of most materials including diamond. With the appropriate choice of process conditions, surface roughness below 1 μm can be attained, and it should be possible to laser mill diamond to a thickness of less than ~50 μm. Ion milling may also be a possibility for the creation of high fidelity features.

(iv) Diamond Etching: Due to its hardness and chemical inertness, etch processing of diamond can present a technical challenge. However, inductively coupled plasma (ICP) etching has been demonstrated with diamond. The ICP technique in particular has several advantages (e.g. no sub-surface damage, production of surfaces with sub-nm rms roughness). By changing the chemical identity of the reactive gas it is possible to switch between isotropic ($Ar/Cl_2$) and anisotropic etches $(Ar/O_2)$[17] (ICP etch rates of up to ~0.2 μm min$^{-1}$ can be achieved[19]). Standard photolithographic procedures can be applied to diamond but the feature size (e.g. depth) is limited by the robustness of the masking material (e.g. photo-resist).

Very thin single crystal diamond plates and structures can be fabricated using a lift-off process employing ion implantation followed by, for example, electrochemical etching.[18] The ion implantation creates subsurface damage in the diamond while the top surface is sufficiently undamaged that a subsequent homo-epitaxial diamond layer can be grown by CVD to a desired thickness. After the CVD growth and processing the underlying damage layer can be etched/removed by an electrochemical or dry etch or even simple annealing[19] to leave a free standing plate of few μm thick and mm×mm lateral dimensions.

The chemical functionality of the diamond surface is also amenable to modification. Using strong acid cleaning procedures, hydrophilic oxygen terminated surfaces are created, whilst exposure to a hydrogen plasma results in hydrophobic hydrogen terminated surfaces. These surfaces can then be used as a starting point for further functionalisation processes using a whole host of chemical or photochemical strategies.

In summary, the applicants have found that by moving to a diamond format, given the outstanding electrical properties of diamond (including much higher resistance than all other competitor materials and lower dielectric loss), improvements in the temporal resolution and noise levels are possible for ion channel measurements. Furthermore the use of etch and milling technologies enables smaller, more robust pore structures of defined reproducible geometry to be fabricated at the single or multiple pore level (mass fabrication). Diamond is also an ideal support material for liquid-liquid electrochemical devices and measurements. Pores can be produced down to the ~nm level, and structures with much larger cone angles, i.e. the angle bisecting the cone, (compared to glass capillaries) to decrease resistance within the pore can be made. It is also possible to produce both H-terminated (hydrophobic) and O-terminated surfaces (hydrophilic) within a single device thus creating perfect environments, for example, oil-water measurements. For particle size analysis the etching and milling procedures developed enable a range of controllable sizes to be produced enabling detection of a wide range of species with varying cross sectional area down to the sub-10 nm level. Given its robustness, in all cases the diamond device is capable of operating under extremes of temperature, voltage and pH conditions. Furthermore, the excellent optical properties means that light activated processes can also be investigated. To this end, the applicants believe that diamond is an ideal substrate material to further advances in the field of chemical. biochemical, and electrochemical analyses.

In many embodiments the diamond film substrate has a thickness, a first face and a second face, the first face being opposite to the second face.

Typically, the pore extends through the diamond film substrate. It is generally the case that the pore has a geometry which is conical, tapered, cylindrical, picture frame (i.e. four sides, which are tapered forming sharp edges at the corners), the shape of an etch pit of [111] facets in a [100] face of the diamond thin film substrate, or hemispherical. The geometry selected will depend upon the intended use of the sensor, for instance the pore may have a geometry which provides a device which yields low capacitance and/or the pore may have a geometry which provides ultra low current leakage.

In some embodiments the device will include more than one pore, there may be just two, three, four, five, six, seven, eight, nine or ten pores, or there may be more than this, for instance 20 to 500, 50 to 250 or 100 to 200 pores. The pores may be randomly distributed across the diamond thin film substrate or arranged in an array. Further, some or all of the pores may be enclosed in an individual chamber and each chamber may be arranged in an array format on support structures. In many examples, each pore will be enclosed.

Often the pore will be of size in the range 1 nm to 100 μm. Often the pore will be a nanopore of size in the range 1 nm to 100 nm, on occasion the pore size will be in the range 5 to 50 nm, often 10 to 30 nm.

In many examples, the thickness of the diamond thin film substrate will be in the range 10 nm to 1 mm, often in the range 20 nm to 500 nm, or in the range 50 nm to 200 nm. In some cases the diamond thin film substrate has a templated or layered structure, with the layers exposed at the inner surface of the pore to introduce functionality for the purpose of chemical, biochemical and electrochemical measurement. Where the structure is layered, it will often comprise layers of diamond of differing conductivities. It may often comprise layers of diamond of differing surface properties which allows selective chemical or physical interactions of a molecule to one of the layers.

The surface of the diamond thin film substrate may be chemically modified with a wide variety of treatments using, for instance, procedures which are known for the surface modification of silicon and silica wafers. In some instances these treatments are selected from silanisation (including silanisation with 3-cyanopropyldimethylchlorosilane), ozonation, surface oxidation, surface halogenation, photochemical attachment of molecules, or a combination thereof. In many embodiments the chemical modification comprises silanisation of the diamond thin film substrate with 3-cyanopropyldimethylchlorosilane. It may be the case that the surface of the diamond thin film substrate has a hydrophilic functionality and a hydrophobic functionality. Often the hydrophilic functionality is on a first face of the diamond thin film substrate and the hydrophobic functionality is on a second face; and a boundary between the first and second face is at a defined location with respect to the pore. In many instances the hydrophilic functionality comprises O-terminated surfaces and/or the hydrophobic functionality comprises H-terminated surfaces.

In some embodiments, a lipid bilayer or monolayer may be deposited on a surface of a diamond thin film substrate. When the lipid layer is present it is preferred that a lipid bilayer be suspended or spanning across the pore. As used herein the term "sensor element" is intended to refer to a part of the device which functions to sense the analyte, often the sensor element will comprise a single or several protein ion channels, or an enzyme, or a molecule that controls the resistance of the bilayer, is inserted into the bilayer that spans the pore opening. In alternative examples, the diamond thin film substrate separates two compartments, each compartment containing electrolyte solutions.

The device may also comprise a means for applying an electric field or voltage between the first face and the second face of the diamond thin film substrate; a means for monitoring the current flow through the nanopore or resistance between the first face and the second face of the diamond thin film substrate, and a means for processing the observed current or resistance to produce a useful output.

The device may also include supporting elements for data acquisition and/or analysis, as would be known to the person skilled in the art.

According to a second aspect of the invention there is provided a method for single molecule detection of an analyte, for the analysis of interactions between a sensor element and an analyte, or for the determination of ion transfer, the method comprising:

providing a solution containing an analyte;
providing a device including a sensor element that recognizes the analyte wherein the sensor element comprises a diamond thin film substrate and a pore which is a nanopore or a micropore included in the substrate;
contacting the device with the solution such that an exterior surface of the sensor element is immersed in the solution and an interior pore surface is contacted by the solution;
applying a voltage across the diamond thin film substrate; and
using the electrical conductivity observed to determine the concentration of the analyte.

This method is essentially a method for sensing analytes, and in many embodiments the sensor element binds to the analyte, this binding event will typically cause a reduction or increase of the current across the sensor element, the change generally ranging from 1 to 100% of the original value. In some applications of the method, the pore will be filled with the solution. It will often be the case that the solution comprises at least one analyte, and a continuous phase selected from electrolytes, organic solvents, gels, biological samples or combinations thereof. In many applications the analyte will be selected from chemical molecules, biological molecules, ions, polymers, lipids, particles and combinations thereof.

In embodiments where the device includes a lipid bilayer deposited on a surface of a diamond thin film substrate, and wherein the lipid bilayer is suspended across a pore, the sensor element may comprise a single protein ion channel that spans the pore opening. Often pressure across the membrane is used to control the rate at which protein ion channels are inserted and removed from the lipid bilayer.

In some applications of the invention, the analyte is a drug candidate, the sensor element is a drug target or modified drug target, and the method is for drug screening. In other applications the analyte is a DNA or RNA species, the sensor element recognises the identity of specific nucleotides and, the method is for nucleic acid sequencing. In yet further applications, the solution comprises two immiscible liquids, these may be selected from aqueous electrolyte solutions in contact with organic solvents containing supporting electrolyte, and aqueous electrolyte solutions in contact with ionic liquids. Where there are two immiscible liquids, an interface between the immiscible liquids may be modified using a modifier selected from, metal nanoparticles, semiconductor nanoparticles, lipids, polymers, ionic and zwitterionic surfactants, conducting polymers, redox polymers, and combinations thereof. In yet further applications, the analyte is an inorganic, metallic or organic particle, or a biological particle, e.g., a virus.

It is known from papers by Taylor et al. that single colour centres in diamond such as negatively charged nitrogen vacancies ($NV^-$) can be used for nano magnetometry[20]. In an application of the invention, the $NV^-$ centre is interrogated optically such that the interaction with the local magnetic field is ascertained. Accordingly, in an embodiment of the invention, the sensor element is the $NV^-$ centre. In such a way the "pore ion current" can be measured via the magnetic field it produces using optical spectroscopy without the need for any electrical connections. The pore could be a "bare" diamond pore or one fabricated using a diamond pore and lipid bi-layer with an ion channel inserted in the pore, as described elsewhere. Furthermore the NV− centre could be used to measure the magnetic properties of a molecule transiting the pore or even trapped in an open or blocked pore. The $NV^-$ centre could be positioned close to a pore by techniques including ion implantation, or the pore could be created in a region of diamond with pre-existing $NV^-$ centres. In addition to measurement of local magnetic fields, currents etc. it is possible to use a single colour centre probe to perform magnetic resonance spectroscopy on systems with unpaired electrons using electron paramagnetic resonance (EPR) or even direct detection of nuclear magnetic resonance (NMR) from molecules/species of interest at sufficiently small pores.

The $NV^-$ centre could be positioned close to a pore by techniques including ion implantation, or the pore could be created in a region of diamond with pre-existing $NV^-$ centres.

Preferred voltages range from 1 microvolt to 5 volts, but often in the 1 millivolt to 1 volt range. The voltage can be applied as a DC or AC signal. Currents will generally range from 100 femptoA to 1 milliA, but most typically in the 1 picoA to 1 μA range.

In the above and further applications of the invention, electrochemical analysis may be combined with spectroscopic measurement to characterize and detect the analyte.

In one example of the invention, the method is a method for the detection of a pore-forming entity. In this embodiment the analyte is a pore-forming entity and the device includes a pore which is a nanopore or a micropore and a bridging means that spans the pore but does not include a sensor element; and wherein the method includes the step of immersing the pore in the solution so that an exterior surface of the pore is immersed in the solution and an interior of the pore is filled with the solution.

Preferred voltages range from 1 microvolt to 5 volts, but often in the 1 millivolt to 1 volt range. The voltage can be applied as a DC or AC signal. Currents range from 100 femptoA to 1 milliA, but most typically in the 1 picoA to 1 μA range.

A third aspect of the invention provides a method of analysis comprising using the device of the first aspect of the invention. The method may be used to analyse a variety of analytes including cells; bacteria; viruses; polymeric particles; ions, molecules; and nanoparticles that are used for formulating and delivery of small molecule, peptide or macromolecular drugs. The analytical method of the invention may also be used for the detection of single molecules, the detection and sequencing of DNA, particle counting, the modelling of drug delivery systems, the study of liquid-liquid interfacial processes, blood analysis, ion transfer voltammetry or potentiometric analysis, and/or the screening of new drugs with protein ion channels. Applications include those in the fields of environmental water analysis, analysis in homeland security sensors, and/or analysis in military applications.

The invention will now be described, by way of example only, by reference to the accompanying drawings, of which:

Figure 5:
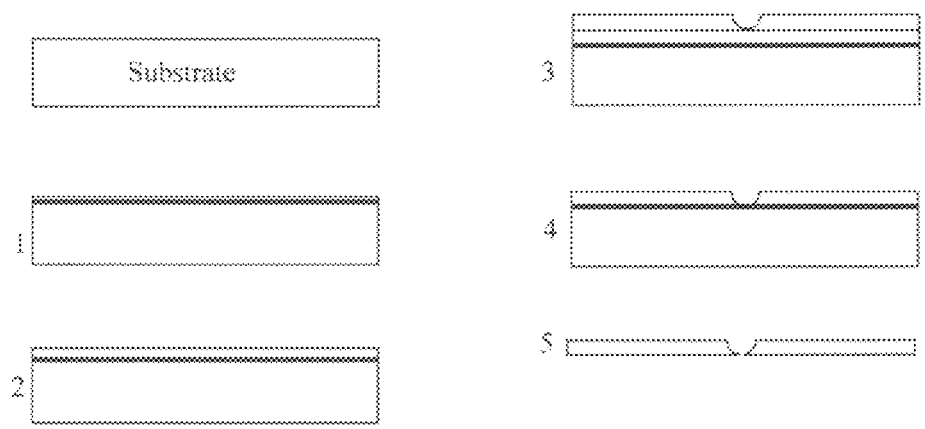
Figure 6:
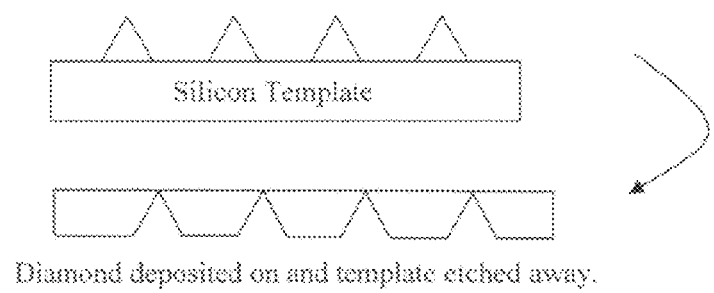
Figure 7:
Figure 8:
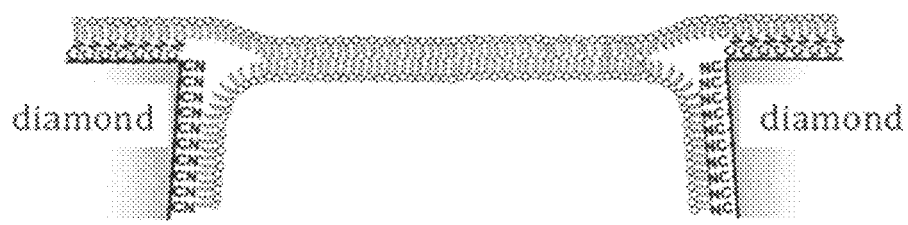
Figure 9:
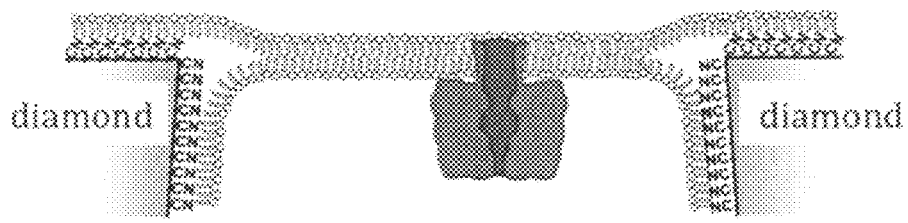
Figure 11:
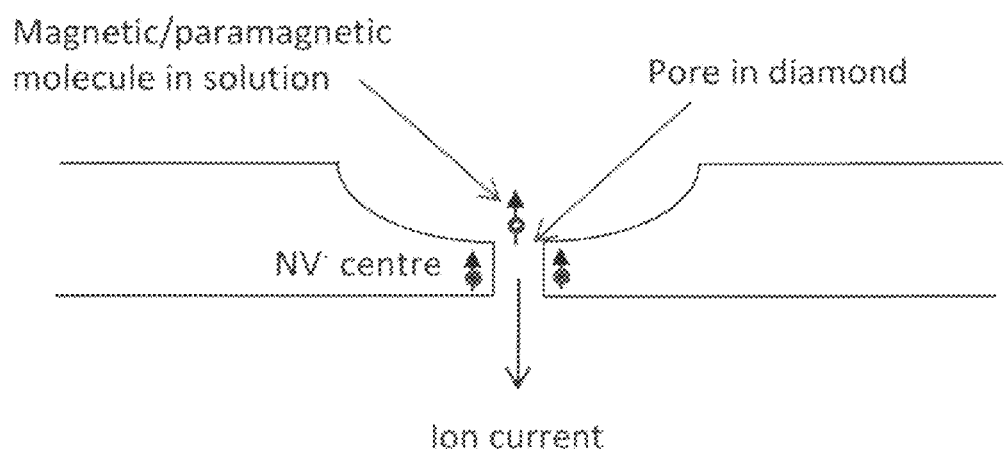
Figure 12A:
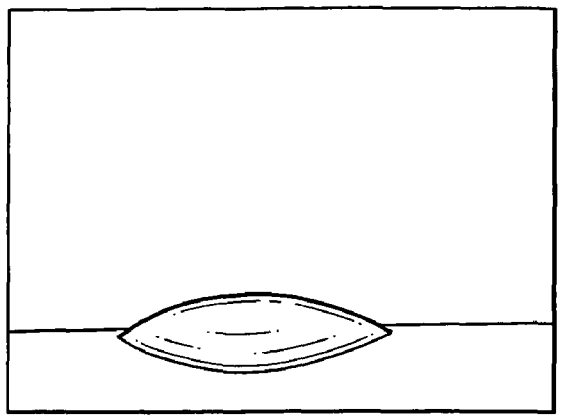
Figure 12B:
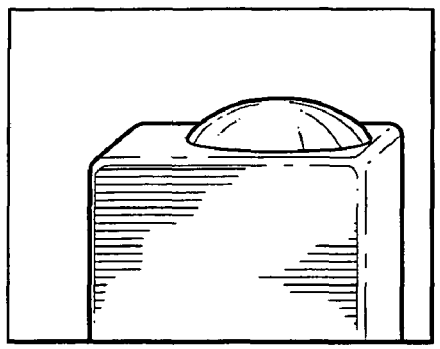
Figure 13:
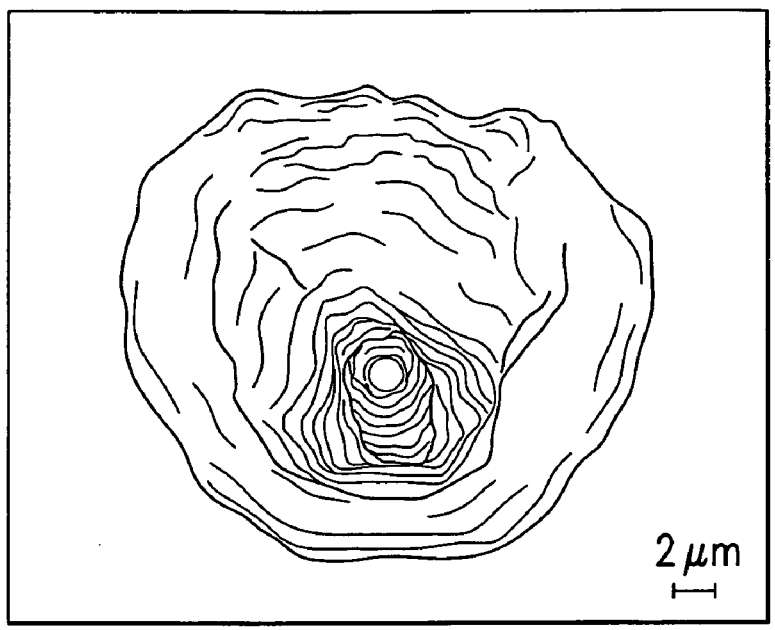
Figure 14:
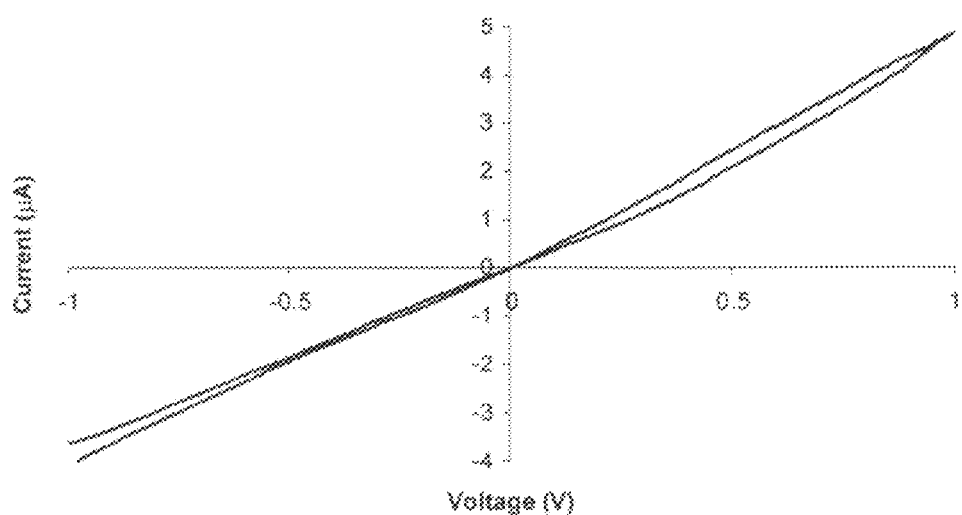

FIG. 5 shows a procedure for the fabrication of hemispherically shaped diamond nanopores comprising steps 1. Implant diamond substrate (for final lift-off). 2. CVD grow the desired thickness of diamond (e.g. 1-10 μm). 3. Spin photoresist or deposit mask material and pattern. 4. Etch, transferring pattern to diamond. 5. Lift off diamond layer. 6. Etch back side to remove damaged diamond (not shown);

FIG. 6 shows a schematic diagram of the production of diamond nanopores from a silicon template;

FIG. 7 shows a ring electrode device formed with a diamond nanopore, the central layer represents a boron-doped region, the outer layers are insulating regions;

FIG. 8 shows a lipid bilayer suspended across a nanopore in a diamond thin film substrate, the diamond surface is chemically modified with 3-cyanopropyldimethylchlorosilane;

FIG. 9 shows a schematic representation of a lipid bilayer suspended across a nanopore in a diamond thin film substrate. In this depicted example, the diamond surface is chemically modified with 3-cyanopropyldimethylchlorosilane and one α-HL has been inserted;

FIGS. 10(a) and (b) show a schematic representation of a DMNP particle analyser based on a nanopore or micropore in a thin film diamond substrate;

FIG. 10(c) shows a schematic representation of the current-time response as particles pass through the pore in the thin film diamond substrate, creating a transient resistive pulse;

FIG. 11 shows a schematic representation of the application of magnetometry to the devices of the invention;

FIGS. 12a and 12b show the droplet formation of water with polycrystalline intrinsic diamond (a) and the droplet formation of water with monolayer functionalised polycrystalline intrinsic diamond (b);

FIG. 13 is a microscope image of a conical pore in accordance with the invention; and FIG. 14 is a current-voltage curve for the pore of FIG. 13.

As used herein the terms "sensor element" and "sensing entity" are intended to be used interchangeably and to refer to the same component of the device. Similarly, the terms "thin film diamond substrate" and "membrane", and the terms "side" and "face" (as applied to the description of the thin film diamond substrate), are intended to have the same meaning and to refer to the same components of the device.

As used herein the term nanopore is intended to refer to pores with small openings of radius 1 μm or less, and the term micropore to refer to pores in the radius range greater than 1 μm.

Figure 2:
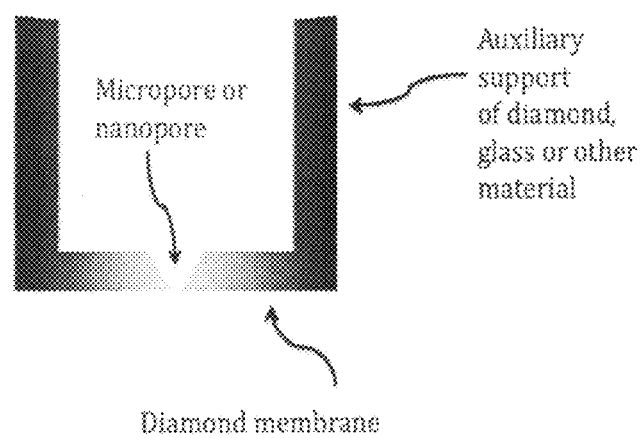
FIG. 2 shows a nanopore fabricated in a diamond thin film substrate.

As noted above, the invention provides a nanopore or micropore sensor device for ion channel recordings (including single molecule detection, biosensors, and DNA sequencing); liquid-liquid measurements (biosensing and ion selective electrodes) and resistive pulse particle counting. The nanopore or micropore device could be described as comprising a nanopore or micropore sensor element or multiple nanopore or micropore sensors elements. The element comprises a diamond thin film substrate and a nanopore or micropore included in the substrate, FIG. 2. The pore will ideally be conical in shape but could also be cylindrical, or hemispherical. The dimensions of the pore can be controlled from ~1 nm to 100 μm. The thickness of the diamond thin film in which the pore is created can also be controlled over the range 10 nm to 1 mm, however of importance is the aspect ratio (hole diameter to length). For example small holes will be easier to fabricate in thinner films. The specific geometry is chosen for different applications. A geometry that yields low capacitance might be fabricated for fast data acquisition measurements (e.g. ion channel recordings or nanometer scale particle counting). A geometry that yields ultra low current leakage might be fabricated for ion selective electrode devices.

Figure 3:
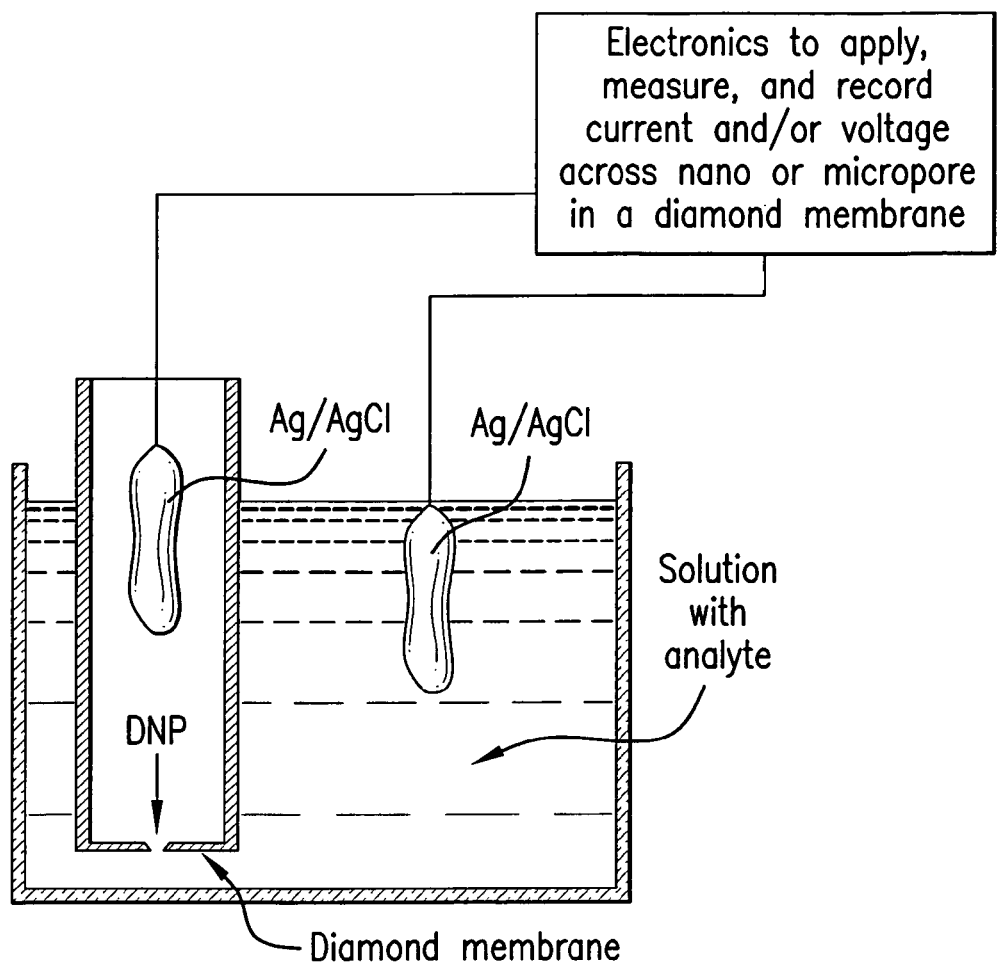
FIG. 3 shows the electrodes and auxiliary electronics which may be used to apply or measure the current or voltage across the pore in the diamond thin film substrate, similar electronics may be extended to an array of pores in a diamond thin film substrate.

The application of diamond micropores and nanopores (DMNP) as sensors in drug screening, DNA sequencing, particle counting, blood analysis, etc. requires additional electronic circuitry to measure analyte interaction with the nanopore. Such a system is schematically depicted in FIG. 3. In such systems, two Ag/AgCl or two $IrO_2$ electrodes, or a Ag/AgCl electrode and an $IrO_2$ electrode, or two other types of electrodes (the same or different), positioned on opposite sides of the membrane may be used to measure the current within the nanopore, or to measure the voltage across the nanopore. The current and voltage readings vary in a known and controlled manner, as analyte interacts with the pore. For instance, the current may decrease temporarily as a particle passes through the nanopore (resistive pulse counting), or the voltage may vary when the nanopore is used as a substrate for an ion selective electrode.

The surface of the DMNP may be chemically modified, for example, to further develop the pore structure or to provide functionality for analytical measurements. For the formation of a suspended bilayer across the nanopore it is often necessary to control the diamond surface chemistry sufficiently such that not only does the lipid form a monolayer but the inner surface of the pore wets sufficiently with aqueous solution. In order to achieve this, a variety of surface functionalization treatments may be employed, including but not limited to, for example, silanisation with 3-cyanopropyldimethylchlorosilane, ozonation, surface oxidation or halogenation, photochemical attachment of molecules, or a combination of surface chemical modifications. Silanisation of flat diamond surfaces with 3-cyanopropyldimethylchlorosilane has been shown to yield a moderately hydrophobic surface (contact angle ~55 degrees), ideal for preparation of a suspended bilayer across the nanopore orifice.[10] For liquid-liquid experiments different strategies will be adopted in the etching and processing steps to produce devices which have both hydrophilic and hydrophobic functionality, including but not limited to e.g. O- and H-terminated surfaces. Solutions containing electrolytes or organic solvents or gels or real biological samples e.g. blood, will be used as the fluid phases in the diamond devices.

Specific examples of nanopore geometries and methods of fabrication include but are not limited to the following examples:

Single or arrays of holes (cylindrical and cone-shaped geometry) in diamond can be laser drilled $\geq 1$ µm in exit diameter, with aspect ratios (length/diameter) $\geq \sim 30$. The spacing can be controlled accurately (to within 1 µm).

For thinner structures, the diamond may be laser milled or etched to produce a "picture frame" structure as described above, this may be ca. <50 µm in thickness, at the thinnest point. If necessary, etch techniques could be used to further smooth the surface. Laser drilling/milling procedures are then employed to produce channels ~1 µm or larger (at the exit point) through diamond <50 µm thick.

Production of defined geometry etch pits with [111] facets on the [100] face of diamond using ICP etch techniques at defect sites.

Figure 4:
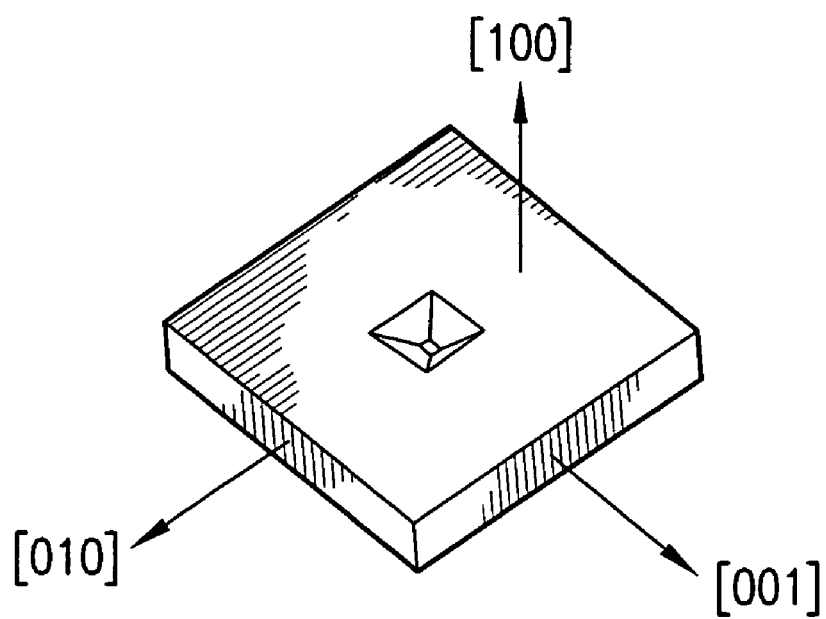
FIG. 4 shows an etch pit nanopore structure on the [100] face of a diamond thin film substrate, the pore being created using ICP.

The etch pit density can be controlled and by varying the thickness of the diamond and the time of the etch, structures of defined geometry, as shown in FIG. 4, with defined pore openings are possible.

DMNPs with openings in the range 100 nm (or smaller)-1 µm, µm's deep and ten's of µm's across can be produced. For example the following steps may be used: 1. Implant diamond substrate (for final lift-off). 2. CVD grow the desired thickness of diamond (e.g. 1-10 µm). 3. Spin photoresist or deposit mask material and pattern. 4. Etch, transferring pattern to diamond. 5. Lift off diamond layer. 6. Etch back side to remove damaged diamond (FIG. 5).

In this way one or many channels in the diamond layer could be produced. The final device may require a support structure. Using this technique functionalized diamond surfaces could be prepared (including different functionalization on both sides).

Templated growth of polycrystalline diamond or nanodiamond on a patterned substrate (FIG. 6). It is possible to make a wide variety of silicon (or silicon oxide) pyramidal tip structures using standard photolithographic procedures. Such a surface could be employed as the substrate for diamond overgrowth.

The thickness of the diamond film grown could be controlled so that it covered the entire tip or a defined height of the tip. Etching away of the substrate (using e.g. HF) would reveal a diamond structure of defined geometry and pore size.

Layered structures. Using CVD techniques it is possible to deposit alternating layers of varying conductivity diamond e.g. intrinsic, boron doped, intrinsic and varying thickness (with the conducting layer as small as few nm in thickness). These structures could be employed in conjunction with the etch/milling techniques described above to produce layered diamond with buried boron doped layers to form back electrodes or channel ring electrodes e.g. FIG. 7.

The structures described above are used in a variety of analytical applications by chemical modification of the surface, deposition of bilayer structures across the pore, by filling the pore with gels and polymers and other chemical materials that introduce functionality.

The key properties of diamond that make is unique and ideal for these applications include: chemical stability and durability; outstanding electrical properties (very high electrical resistivity, moderate dielectric constant, low dielectric loss tangent); transparent in the UV (225 nm) to far IR regions; biocompatibility and reproducible and mass fabrication.

There are many possible applications of the invention, some examples are described below:

Ion Channel Recordings and DNA sequencing. In certain embodiments, to effectively deposit a lipid layer or bilayer on a diamond membrane, the exterior and/or interior surface of the DMNP may need to be chemically modified to obtain a moderately hydrophobic surface. For example, the diamond surface may be modified by a variety of diamond-reactive species, e.g. 3-cyano-propyldimethylchlorosilane that reacts with the—OH groups of the diamond surface, following oxidation of the surface. Changing the surface properties from that of bare diamond, either hydrophobic (H-terminated) or hydrophilic (O-terminated), to a moderately hydrophobic surface induces the hydrophobic part of a lipid molecule to point towards the surface when it is deposited on the surface. In particular, when the interior and exterior surfaces of a DMNP are rendered partially hydrophobic, deposition of a lipid monolayer on the diamond surface spontaneously yields a bilayer across the opening of the nanopore. That is, at the opening of the pore, the lipid monolayer evolves into a lipid bilayer, while the lipids deposited on the exterior surface and interior surface still assume a monolayer structure. This transition between the lipid monolayer on the exterior surface and the lipid bilayer across the nanopore opening is a consequence of the chemical modification of the surfaces (FIG. 8).

In certain embodiments, as described above, the invention provides a method for single molecule detection of an analyte or for analysis of interactions between a sensing entity and an analyte. The method may comprise: providing a sample solution containing an analyte of interest; providing a nanopore device including a sensing entity that recognizes the analyte; contacting the nanopore device with the solution such that the exterior surface of the nanopore is immersed in a solution and the interior nanopore surface is contacted by a solution, whether either solution contains the molecule or analyte of interest; applying an appropriate voltage across the two sides of the membrane; and analyzing the electrical conductivity to determine the concentration of the analyte of interest.

The analyte may be any entity that is recognizable by the sensing entity. Such analytes may include but are not limited to chemical or biological molecules, ions, polymers, lipids, particles, etc. When the sensing entity binds to the analyte, the binding event causes a reduction of current across the sensing entity. The current through the means sensing entity can be measured by using either alternating current (AC) or direct current (DC) measurements.

The invention provides a fundamental advantage in sensing and sequencing applications due to the very high mechanical and electrical stability of bilayers formed on the DMNP membranes. For instance, with glass nanopores, high electrical voltages (~1 V) can be applied across the device with lipid bilayer supported ion channels as the sensing entity, allowing applications not assessable using conventional ion channel recording cells (~0.24 V limit). The mechanical stability allows devices with lipid bilayer supported ion channels to be transported and to be used in microfluidics systems. These advantages will extend to diamond substrates. The combination of the very high mechanical and electrical stability of bilayers formed on DMNP membranes with the chemical stability and biocompatibility greatly extends the lifetime of the devices in numerous applications.

Figure 1:
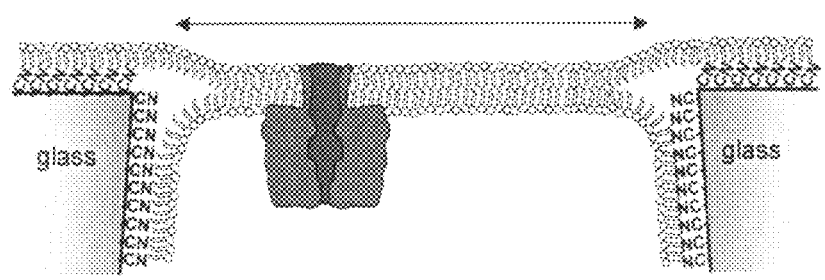
FIG. 1 shows a schematic representation of a lipid bilayer suspended across a nanopore in a glass substrate, the diamond surface is chemically modified with 3-cyanopropyldimethylchlorosilane and one α-HL has been inserted.

In certain embodiments, a modified DMNP corrals a single protein ion channel as the sensing entity, for instance, α-hemolysin (αHL), in the lipid bilayer region that spans the diamond nanopore opening. The bilayer structure may span over the modified diamond nanopore, FIG. 9 is such that current can only flow through the protein ion channel. FIG. 1 shows an equivalent system using known, glass, technologies. The protein ion channel is able to diffuse in the bilayer above the pore opening but cannot leave this area to enter the lipid monolayer. While an analyte is recognized by the ion channel and/or passes through ("translocates") the ion channel, it partially blocks ionic current through the pore. This blockade is measured by a transient increase in ionic resistance (or decrease in ionic current). The binding rate of the analyte may provide concentration of the analyte and/or affinity data of the analyte with the sensing entity.

In certain embodiments, the transmembrane pressure may be used to control the rate of which protein ion channels are inserted and removed from the lipid bilayers deposited on the DMNP membrane, as discussed by White et al.[8] The pressure can be used to control the number of ion channels (single vs multiple channels), and to insert/remove channels at preselected times. This ability allows different protein ion channels to be inserted at different locations in a DMNP-based array sensor when placed in contact with a common solution, or sequentially with time in different solutions.

As described above, in certain embodiments, the invention provides a method for drug screening. The method may comprise: providing a sample solution containing a drug candidate; providing a nanopore device including a sensing entity that is a drug target or a modified drug target; contacting the nanopore device with the solution such that the exterior surface of the nanopore is immersed in the solution and the nanopore is filled with the solution; applying an appropriate voltage across the two sides of the membrane; and analyzing the electrical conductivity to determine whether an interaction occurs between the drug target and the drug candidate and/or the affinity of the drug candidate with the drug target.

Also described are embodiments where, the invention provides a method for nucleic acid sequencing, the method may comprise: providing a sample solution containing a DNA or RNA species; providing a nanopore device including a sensing entity that recognizes the identity of specific nucleotides; contacting the nanopore device with the solution such that the exterior surface of the nanopore is immersed in the solution and the nanopore is filled with the solution; applying an appropriate voltage across the two sides of the membrane; and analyzing the electrical conductivity to determine sequence of the DNA or RNA molecule. For example, as a DNA molecule passes through the protein ion channel included in a nanopore sensing device, a characteristic change in the ion channel conductance is associated with different nucleotides. By monitoring the time dependent conductance of the protein as the DNA passes through it, the nanopore sensing device may sequence a strand of DNA from just a couple bases in length up to hundreds of thousands bases in length.

In certain embodiments, the invention provides a method for detection of a pore-forming entity, as described above, the method may comprise: providing a sample solution that may contain a pore-forming entity; providing a nanopore device that includes a means that span across the nanopore but does not include a sensing entity; contacting the nanopore device with the solution such that the exterior surface of the nanopore is immersed in the solution and the nanopore is filled with the solution; applying an appropriate voltage across the two sides of the membrane; and analyzing the electrical conductivity to determine whether the pore-forming entity is present in the solution and/or the amount of the pore-forming entity in the solution. Presence of a pore-forming entity increases the electrical conductivity across the two sides of the nanopore.

Nano- and Micro-particle Counting and Analysis: Particle counting based on resistive pulse counting (or "electrozone sensing") is a common method of particle analysis and is the basis of commercial Coulter Counters. In 1970s, DeBlois et al. reported the first use of a sub-µm cylindrical pore etched in a plastic membrane in the detection of nanometer-sized particles (45 nm in radius).[21] More recently, Crooks' group reported the applications of $Si_3N_4$ or PDMS supported epoxy membranes containing individual multi-walled carbon nanotube (~65 nm in radius); particles with different size and surface charge were simultaneously analyzed.[22] Sohn's group showed the successful application of micro-fabricated nanopores/channels in quartz substrate/PDMS membranes in counting of nanoparticles (as small as 43 nm in radius, ~0.16 pM) and biological molecules, and in the sensing of biological interactions.[23] Other techniques, such as dynamic light scattering[24] and field-flow fractionation (FFF),[25] have been successfully applied in the analysis of nanoparticles.

Also described here is a diamond nanopore device for particle counting and analysis, the device often comprising: a diamond membrane having a thickness, having a first and second side, the first side being opposite to the second side, and having a nanopore extending through the membrane over the thickness of the membrane. Typically, the diamond membrane containing a nanopore separates two compartments, which two compartments typically contain electrolyte solutions. The device may further comprise a means for applying an electric field between the first side and the second side of the membrane; a means for monitoring the current flow through the nanopore or resistance between the first side and the second side of the membrane, and a means for processing the observed current or resistance to produce a useful output. Various embodiments of the nanopore device may be incorporated into larger device structures that provide supporting elements for, for example, data acquisition and analysis. The membrane may be configured to include more than one nanopore, or an array of nanopores. Each individual nanopore may be enclosed in an individual chamber and such individual chambers may be arranged in an array format on suitable support structures.

Figure 10:
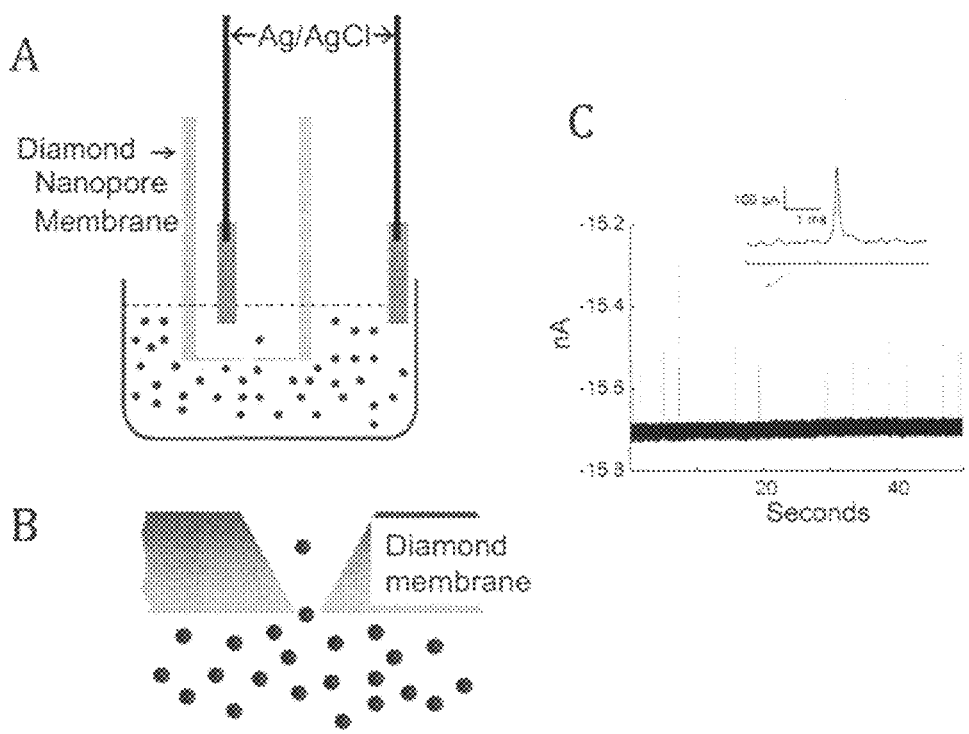

FIG. 10 is a schematic of a DMNP particle analyzer. The diamond membrane is often an integral part of chamber. The nanopore is generally included in diamond membrane and is usually of a conical shape, with the smaller opening of the nanopore contacting sample containing particles to be analyzed. The smaller opening of the nanopore ranges from 2 nm to 500 nm. A voltage is applied between electrodes and to drive an ionic current through the nanopore. Particles passing through nanopore are readily detected by measuring the transient change in the electrical resistance, or electrical conductivity of nanopore. As particles pass through the nanopore, a short transient decrease in the current is observed. The frequency of these resistive pulses is proportional to the particle concentration, while the magnitude and shape of the pulse provides the nanoparticle shape and size. The shape and duration of the pulse can be used to determine the shape, size, and/or charge of a particle. Frequency of pulses may also indicate the concentration of a particle. This method can be used to determine the concentration, the shape, the size and electrical charge of the particles. DC or AC voltage may be applied via the electrical field applying means. Typical DC voltage ranges from about 10 to about 500 mV. Typical AC voltage ranges from about 2 to about 25 mV rms.

The diamond based nanopore particle analyzer is ideal for analysis of particles in the 2-100 nm range, but may be used for measurement of particles smaller than 2 nm or bigger than 100 nm. Various particles, including but not limited to cells, bacteria, viruses, polymeric particles, ions, molecules, and nanoparticles that are used for formulating and delivery of small molecule, peptide or macromolecular drugs can be tested. The nanopore particle analyzer can also be used in environmental water analysis and as sensors in homeland security and military applications. Exploitation of the present invention will be driven by the explosive growth of new technologies based on nanoparticles and by new regulations in environmental monitoring.

Nano magnetometry: Magnetometry can be used to interrogate the negatively charged nitrogen centres in diamond ($NV^-$ centres), FIG. 11 is a schematic representation of the magnetic field local to the pore of the sensor device. The arrows within a diamond structure represent the local magnetic field and the arrow passing through the pore represents the ion current through the pore. A schematic magnetic/paramagnetic molecule is illustrated passing through the pore. This technique has the advantage that the interrogation of the $NV^-$ centres is via optical spectroscopy and hence the pore current can be determined without the need for electrical connections. As the pore current will be modified by molecule with magnetic properties passing through the pore, the presence of these molecules can be determined and their motion studied.

Electroanalysis at liquid/liquid interfaces: A key feature of the diamond membranes is the potential for the production of one face hydrophobic and the other hydrophilic, with the boundary between the two at a defined location with respect to the pore (for example, at either face of the membrane—at the entrance to the pore—or somewhere along the length of the pore). This can lead to an array of very well-defined and stable liquid/liquid interfaces. The pore may be either conical or tapered (see above) depending on the particular application. The membrane may be used with a wide range of mutually immiscible liquids, such as: aqueous electrolyte solutions in contact with organic solvents or gels (e.g. nitrobenzene or 1,2-dichloroethane or other organic solvents) containing supporting electrolyte; aqueous electrolyte solutions in contact with ionic liquids. In usual practice the arrangement would be such that the organic phase/ionic liquid wetted one face and the whole of the inside of the pores. The organic phase or ionic liquid phase may also be gelled to provide further mechanical stability. The aqueous sample may also be a biological fluid, such as blood, blood plasma, urine, saliva, etc.

For many applications, the set up comprises two electrodes, one located in either liquid phase, which can be used to apply a potential across the interface. These electrodes are also used to measure the current. For situations where there are relatively large currents (e.g. >1-10 or greater), a 4-electrode system may be employed in which an electrode in the bulk of each phase is used to measure/drive a current, which another electrode in each phase (close to the interface) is employed to determine the interfacial potential drop.

A major application of these membranes is to determine ion transfer, via ion transfer voltammetry. In this case, the organic or ionic liquid phase is often on one side of the DMNP and the second phase is the solution to be analysed (aqueous sample, e.g. natural water, lake water, sea water, effluent etc.; biological fluid as named above). The organic phase may include a particular ionophore, or other complexing agent, which interacts with the ion of interest (e.g. a crown ether or other ligand), as well as supporting electrolyte, but also may not (depending on the application). A constant potential is applied, or the potential is scanned or pulsed with an arbitrary waveform to induce the transfer of the ion from the aqueous sample to the organic phase and the current is measured (as a function of time and/or potential). The amperometric analysis may also be carried out under conditions where the ion is accumulated from the aqueous sample into the organic/ionic liquid phase for a predetermined time and then stripped out via a change in the potential. The device may be employed in either stationary solution or under flow conditions. The analysis is applicable to simple ions, such as $Ca^{2+}$, $K^+$, $Na^+$ (and total salt analysis), and more complex ions such as ionisable drug molecules, DNA fragments and proteins. In certain instances, the ion may not transfer across the interface, but will be accumulated at the interface. Here, a stripping analysis protocol (or impedance analysis) will generally be employed to determine the amount of material deposited. This approach may be used for some complex ions and also charged particles, providing a means of particle counting that complement the approach already described.

With similar apparatus it is possible to carry out electron transfer reactions across the interface between the two immiscible electrolyte solutions. In this case, the organic phase or ionic liquid phase contains either an electron donor or electron acceptor. By tuning the applied potential across the interface, it is possible to drive selective interfacial electron transfer processes between these molecules in the organic (or ionic liquid) phase and particular analytes in the aqueous phase. The corresponding current response is used for analysis. For example, one can analyse for various antioxidants and other molecules in this way. In some cases, for example where the analyte of interest is a lipophilic organic molecule, the analyte may be in an organic phase and the aqueous phase will contain the electron donor or acceptor (for detection by electron transfer), or serve as a sink for detection via ion transfer.

The interfaces described can be modified to enhance the selectively and expand the range of molecules and ions that can be detected. Modifiers include: metal nanoparticles (either pre-formed or deposited from metal ions directly at the pores of the membrane); semiconductor nanoparticles; lipids; polymers; ionic and zwitterionic surfactants; conducting polymers; redox polymers. Metal and semiconductor nanoparticles may be employed to enhance electron transfer across the liquid/liquid interface for some of the analyses described, facilitating the detection, for example of oxygen. There is further scope for carrying out analysis via spectroelectrochemistry, in which the current response is coupled to a spectroscopic measurement, including UV-visible spectroscopy, and fluorescence (including confocal measurements). Electrochemical analyses accompanied by the generation of light (e.g. for the detection of various anti-oxidants), via electrogenerated chemiluminescence will be powerful and sensitive due to the excellent optical properties of the diamond membranes, already highlighted.

Potentiometric measurements may also be realised with the diamond membrane, either with the two phase liquid/liquid geometry of the type already described or with a three-phase system in which the pores in the membrane are modified with an ion selective polymer matrix (or organic solution), which separates an aqueous solution containing a reference electrode (e.g. Ag/Ag/Cl) from an analyte solution which is contacted by a second reference electrode.[26] By measuring the potential between the two electrodes, one can obtain information on ion concentrations in the sample. One can also carry out combined amperometric/potentiometric measurements with this type of device.

EXAMPLES

Example 1

Functionalisation of Diamond Surface

It has been shown using contact angle measurements and confocal microscopy that the surface of the diamond can be successfully modified. In this example the surface modification was using the silanising agent 3-cyanopropyldimethylchlorosilane.

The observational techniques employed were standard techniques, known to those skilled in the art.

FIGS. 12a and 12b are photographs showing the contact angle of water with the polycrystalline intrinsic diamond prior to functionalisation)(31.3°) and after functionalisation with 3-cyanopropyldimethylchlorosilane)(52.4°), this change in contact angle results from the formation of a monolayer of 3-cyanopropyldimethylchlorosilane on the diamond surface.

Example 2

Pore Formation

The polycrystalline intrinsic diamond was also percussion laser drilled to produce a pore. In this example the pore prepared was conical and of size around 6-8 μm at the widest part of the cone and around 1 μm at the exit, as can be seen from the microscope image in FIG. 13.

A current-voltage curve was derived for this system, FIG. 14. The curve correlated to that expected for conical pore systems and was obtained using two silver/silver chloride reference electrodes placed on either side of the pore and the current passing across the pore was measured as a function of applied voltage in a solution containing 1 M KCl and 10 mM phosphate buffered saline solution (PBS).

The ability to measure the current passing across the pore allows for the sensing of a wide range of analytes passing through the pore as they will alter the current during transition.

It should be appreciated that the devices and methods of the invention are capable of being incorporated in the form of a variety of embodiments, only a few of which have been illustrated and described above.

REFERENCES

1. Dekker, C. *Solid State Nanopores, Nature Nanotechnology,* 2007, 2, 209-215
2. Fertig, N. et al, *Activity of single ion channel proteins detected with a planar microstructure Acc. Phys. Lett.* 2002, 81, 4865-4867
3. Deamer, D. W., Branton, D. *Characterisation of Nucleic Acids by Nanopore Analysis, Ace. Chem. Res.* 2002, 35, 817-825
4. Kasiananowicz, J. J., Branton, D., Deemer, D. W. *Characterisation of Individual Polynucleotide Molecules Using a Membrane Channel, Proc. Natl. Acad. Sci.* 1996, 93, 13770-13773
5. Bayley, H., Martin, C. R, *Resistive-Pulse Sans From Microbes to Molecules Chem. Rev.* 2000, 100, 2575-2594
6. Shaffer, C., Genetic Engineering and Biotechnology News, 2005, 25, 1-3
7. Akeson at al, *Microsecond time-scale discrimination among polysytidylic acid, polyadneylic acid and polyuridylic acid as homopolymers or as segments within single RNA molecules, Biophys. J.* 1999, 77, 3227-3233
8. White R. J. et al *Single ion-channel recordings using glass nanopore membranes, J. Am. Chem. Soc.* 2007, 129, 11766-11775
9. Leich, M. A., Richmond, G. L. *Recent Advances in Studies of Liquid-Liquid Interfaces. Faraday Discussions* 129 (2005) 1
10. Taylor. G, Girault, H. H. J. *Ion Transfer Reactions across a Liquid-Liquid Interface Supported on a Micropipette Tip. J. Electroanal. Chem.* 208 (1986) 179
11. Campbell, J. A., Girault, H. H. *Steady stale current for ion transfer reactions at a micro liquid/liquid interface, J. Electroanal. Chem.* 266 (1989) 465
12. Zazpe, R., Hibert, C., O'Brien, J., Lanyon, Y. H., Arrigan, D. W. M. *Ion transfer voltammetry at silicon membrane based arrays of micro liquid-liquid interfaces, Lab on a Chip* 7 (2007) 1732
13. Lines, R. W. *Particle Size Analysis*, Stanley-Wood, N. G. and Lines, R. W., Eds.
14. DeBlois, R. W., Bean, C. P. *Counting and Sizing of Submicron particles by resistive pulse technique, Rev. Sci. Instrum.* 7 (1970) 909
15. Li, L, Gershow, M., Stein, D., Brandin, E., Golovehenko, J. A. *DNA molecules and configurations in a solid state nanopore microscope, Nat. Mater.* 2 (2003) 611
16. Brandon, J R; Coe, S E; Sussmann, R S, et al. *Development of CVD diamonds r.f. windows for ECHR, Fus. Eng. Design* 2001, 53, 553-559
17. Lee, C L; Gu, E et al *Micro-cylindrical and micro-ring lenses in CVD diamond*, Diamond. Rel. Mater. 2007, 16, 944-948
18. Hunn, J. D.; Withrow, S. P.; White, C. W. et al. *The separation of thin single crystal from bulk diamond by MeV implantation, Nuc. Instrum. Methods in Phys Res. B; Beam Inter. Mater. Atoms,* 1995, 99, 602-605
19. see for example patent 'Separation of Grown Diamond from Diamond Seeds Mosaic US2007017437
20. J. M. Taylor, P. Cappellaro, L Childress, L hang, D. Budker, P. R. Hemmer, A. Yacoby, A. Walsworth & M. D. Luken, *Nature Physics*, 2008, 4, 810
21. DeBlois, R. W. and Bean, C. P. *Counting and sizing of submicron particles by resistive pulse technique, Rev. Sci. Instrum.* 1970, 41, 909-916; DeBlois, R. W. and Wesley, R. K. A. *Sizes and concentrations of several type-c oncornaviruses and bacteriophage-t2 by resistive-pulse technique J. Virol.* 1977, 23, 227-233; and DeBlois, R. W. and Bean, C. P.; Wesley, R. K. A. *Electrokinetic measurements with submicron particles and pores by resistive pulse technique, J. Colloid Interface Sci.* 1977, 61, 323-335
22. Ito, T., Sun, L., Henriques, R. R. and Crooks, R. M. *A carbon nanotube based Coulter nanoparticle counter, Acc. Chem. Res.* 2004, 937-945
23. Saleh, O. A. and Sohn, L. L. *An artificial nanopore for molecular sensing, Nano Lett.* 2003, 3, 37-38
24. Russel, W. B., Saville, D. A. and Schowalter, W. R. *Colloidal Dispersions*, Cambridge University Press, New York, 1989
25. Giddings, J. C. *Unified Separation Science*. John Wiley & Sons, Inc. 1991
26. Shim, J. H.; Kim, J.; Cha, G. S.; Nam, H.; White, R. J., White, H. S. and Brown, R. B, *Glass Nanopore Based Ion Selective Electrodes, Anal. Chem.* 2007, 79, 3568-3574

The invention claimed is:

1. A sensor device for an application selected from ion channel recordings; liquid-liquid based sensors and resistive pulse particle counting, the sensor device comprising;
   at least one sensor element, the element comprising a diamond thin film substrate, a surface of which is chemically modified; and
   a pore which is a nanopore or a micropore included in the substrate;
   wherein the diamond thin film substrate has a templated or layered structure wherein the layered structure comprises layers of diamond of differing conductivities, and wherein the sensor device further comprises two electrodes positioned on opposite sides of the diamond thin film substrate and configured to measure a current within the pore or to measure a voltage across the pore.

2. A device according to claim 1 wherein the diamond thin film substrate has a thickness, a first face and a second face, the first face being opposite to the second face.

3. A device according to claim 1 wherein the pore has a conical, tapered, cylindrical, picture frame, etch pit of [111] facets in a [100] face of the diamond thin film substrate, or hemispherical geometry.

4. A device according to claim 1 comprising more than one pore, in an array of pores.

5. A device according to claim 4 wherein each pore is enclosed in an individual chamber and each chamber is arranged in an array format on support structures.

6. A device according to claim 1 wherein a surface of the diamond thin film substrate has been chemically modified with a treatment selected from silanisation with 3-cyanopropyldimethylchlorosilane or other silanes, ozonation, surface oxidation, surface halogenation, photochemical attachment of molecules, or a combination thereof; and/or wherein the surface of the diamond thin film substrate has a hydrophilic functionality and a hydrophobic functionality.

7. A device according to claim 6 wherein the hydrophilic functionality is on a first face of the diamond thin film substrate and the hydrophobic functionality is on a second face; and wherein a boundary between the first and second face is at a defined location with respect to the pore; and/or wherein the hydrophilic functionality comprises O-terminated surfaces and/or the hydrophobic functionality comprises H-terminated surfaces.

8. A device according to claim 1 wherein the diamond thin film substrate separates two compartments, each compartment containing electrolyte solutions.

9. A method for single molecule detection of an analyte, for the analysis of interactions between a sensor element and an analyte, or for the determination of ion transfer, the method comprising:

providing a solution containing an analyte;

providing a device including a sensor element that recognizes the analyte wherein the sensor element comprises a diamond thin film substrate and a pore which is a nanopore or a micropore included in the substrate;

contacting the device with the solution such that an exterior surface of the sensor element is immersed in the solution and an interior pore surface is contacted by the solution;

applying a voltage across the diamond thin film substrate; and measuring a current within the pore or a voltage across the pore to determine the concentration of the analyte;

wherein the diamond thin film substrate has a templated or layered structure wherein the layered structure comprises layers of diamond of differing conductivities, and wherein the device further comprises two electrodes positioned on opposite sides of the diamond thin film substrate and to measure the current within the pore or to measure the voltage across the pore.

10. A method according to claim 9 wherein the sensor element binds to the analyte and the binding event causes a reduction of current across the sensor element.

11. A method according to claim 9 wherein the solution comprises two immiscible liquids selected from, aqueous electrolyte solutions in contact with organic solvents containing supporting electrolyte, and aqueous electrolyte solutions in contact with ionic liquids.

12. A method according to claim 11 wherein an interface between the immiscible liquids is modified using a modifier selected from, metal nanoparticles, semiconductor nanoparticles, lipids, polymers, ionic and zwitterionic surfactants, conducting polymers, redox polymers, and combinations thereof.

13. A method according to claim 11 wherein electrochemical analysis is combined with spectroscopic measurement.

* * * * *